United States Patent [19]

Elias et al.

[11] Patent Number: 4,720,866

[45] Date of Patent: Jan. 19, 1988

[54] COMPUTERIZED STETHOSCOPIC ANALYSIS SYSTEM AND METHOD

[75] Inventors: Antonio L. Elias, Lexington, Mass.; Mark F. Davis, Pacifica, Calif.

[73] Assignee: Seaboard Digital Systems, Inc., Prince Edward Island, Canada

[21] Appl. No.: 778,524

[22] Filed: Sep. 20, 1985

[51] Int. Cl.$^4$ .............................................. A61B 7/00
[52] U.S. Cl. ........................................ 381/67; 128/709
[58] Field of Search .......................... 381/67, 58, 48; 128/709, 710, 715, 773; 364/415, 417; 324/77 E

[56] References Cited

U.S. PATENT DOCUMENTS

| | | | |
|---|---|---|---|
| 1,686,504 | 10/1928 | Dodge et al. | 381/67 |
| 2,356,262 | 8/1944 | Mott | 381/67 |
| 2,400,662 | 5/1946 | Roberton et al. | 381/67 |
| 3,122,208 | 5/1964 | Dymski et al. | 381/67 |
| 3,396,241 | 8/1968 | Anderson et al. | 381/67 |
| 3,409,737 | 11/1968 | Settler et al. | 381/67 |
| 3,651,798 | 3/1972 | Egli et al. | 381/67 |
| 3,790,712 | 2/1974 | Andries | 381/67 |
| 3,930,560 | 1/1976 | Carlson et al. | 381/67 |
| 4,167,223 | 9/1979 | Liesse | 381/67 |
| 4,193,393 | 3/1980 | Schlager | 128/710 |
| 4,220,160 | 9/1980 | Kimball et al. | 381/67 |
| 4,226,248 | 10/1980 | Manoli | 381/67 |
| 4,295,471 | 10/1981 | Kaspari | 381/67 |
| 4,362,164 | 12/1982 | Little et al. | 381/67 |
| 4,428,381 | 1/1984 | Hepp | 128/773 |
| 4,483,346 | 11/1984 | Slavin | 128/710 |
| 4,528,689 | 7/1985 | Katz | 381/67 |
| 4,586,514 | 5/1986 | Schlager | 128/773 |

FOREIGN PATENT DOCUMENTS 307787 10/1952 Switzerland .
386066 2/1933 United Kingdom .

OTHER PUBLICATIONS

Blinowska, et al., "Computer Analysis of Frequency Spectrum . . . ", *Medical & Biol. Engineering and Computing*, vol. 17, Mar. 1979, pp. 207–210.
"Use Voiceprints to Analyze Speech" by Steve Ciarcia, Glastonbury, CT 06033, BYTE Publications, Inc., Mar. 1982, pp. 50–64.

*Primary Examiner*—Jin F. Ng
*Assistant Examiner*—L. C. Schroeder
*Attorney, Agent, or Firm*—Kenway & Crowley

[57] ABSTRACT

This invention relates in general to a method and apparatus for identifying specific medical conditions from detected stethoscopic sounds. More particularly, the invention relates to the processing of such sounds electronically and the display of the time-variations of the spectral composition of such sounds. The invention is embodied in an accessory package designed to enable a host computer to perform computerized stethoscopic analysis.

3 Claims, 10 Drawing Figures

COMPUTERIZED STETHOSCOPIC ANALYSIS SYSTEM AND METHOD

BACKGROUND OF THE INVENTION

Nothing is more symbolic of traditional medical practice than the stethoscope. Because it is easily portable, relatively inexpensive, and requires no input power to operate, it has long been considered an ideal instrument. Nevertheless, there is frequent need for something more than a quick, qualitative analysis, and, in response to that need, various electronic advances have been utilized to improve the performance of the stethoscope. Generally, however, the very nature of the problem has inhibited the development of a truly satisfactory electronic stethoscope.

First, the signals being sought are almost invariably of the type which are lost in ambient noise, and isolating them from that noise in any useful form has proven difficult. Second, with some of the available electronic devices, too much is left to the skill of the practitioner for auscultation diagnosis.

It is, therefore, a primary object of the present invention to analyze electronically and display objectively evidence of medical conditions represented by sounds produced by organs of the human body.

It is a further object of the invention to enable diagnosis of certain medical conditions with an instrument which is non-invasive and passive.

Another object of the invention is to improve auscultation diagnosis utilizing computerized digital signal-processing techniques.

Still another object of the invention is to analyze sounds produced by organs of the human body for evidence of patterns and to display in a distinctive manner any departures from these patterns.

A still further object of the invention is to produce permanent, objective, medical and legal records of auscultation analysis.

A more specific object of the invention is the provision of an accessory package which enables a general-purpose computer to perform computerized stethoscopic analysis.

SUMMARY OF THE INVENTION

The accomplishment of the foregoing objectives results from detection of sound from the body, such as lung sound, by an electronic transducer and conversion of that sound to a series of spectra taken consecutively at small time intervals. The body sounds may be recorded for later input to the accessory device of the invention or may be directly applied from a microphonic pick-up in real time. The lung sound spectra are then displayed as regions of light varying in brightness with the signal strength of each frequency. The light patterns are displayed in rows, one below the other, to form a two-dimensional picture of the changing frequency content of the sounds. Finally, the spectra are examined for evidence of anomalous change.

Basically, what is involved is an accessory package for use with a general-purpose microcomputer having appropriate software and hardware to acquire, analyze, and display stethoscopic data. The accessory includes an input device which may be either an audio recording unit on which data has been prerecorded or a microphonic transducer which picks up sound present at the skin of a patient. The audio signal is pre-amplified and conditioned for application to a bank of fixed-center-frequency electronic filters. The output of each filter is sampled and converted to digital form by an analog-to-digital converter, the output of which is processed in the general purpose microcomputer for analysis and display on a CRT screen or recording in a hard-copy device.

For a better understanding of the present invention, reference should be made to the following description of a preferred embodiment and the appended drawing in which:

DESCRIPTION OF PREFERRED EMBODIMENT

Figure 1:
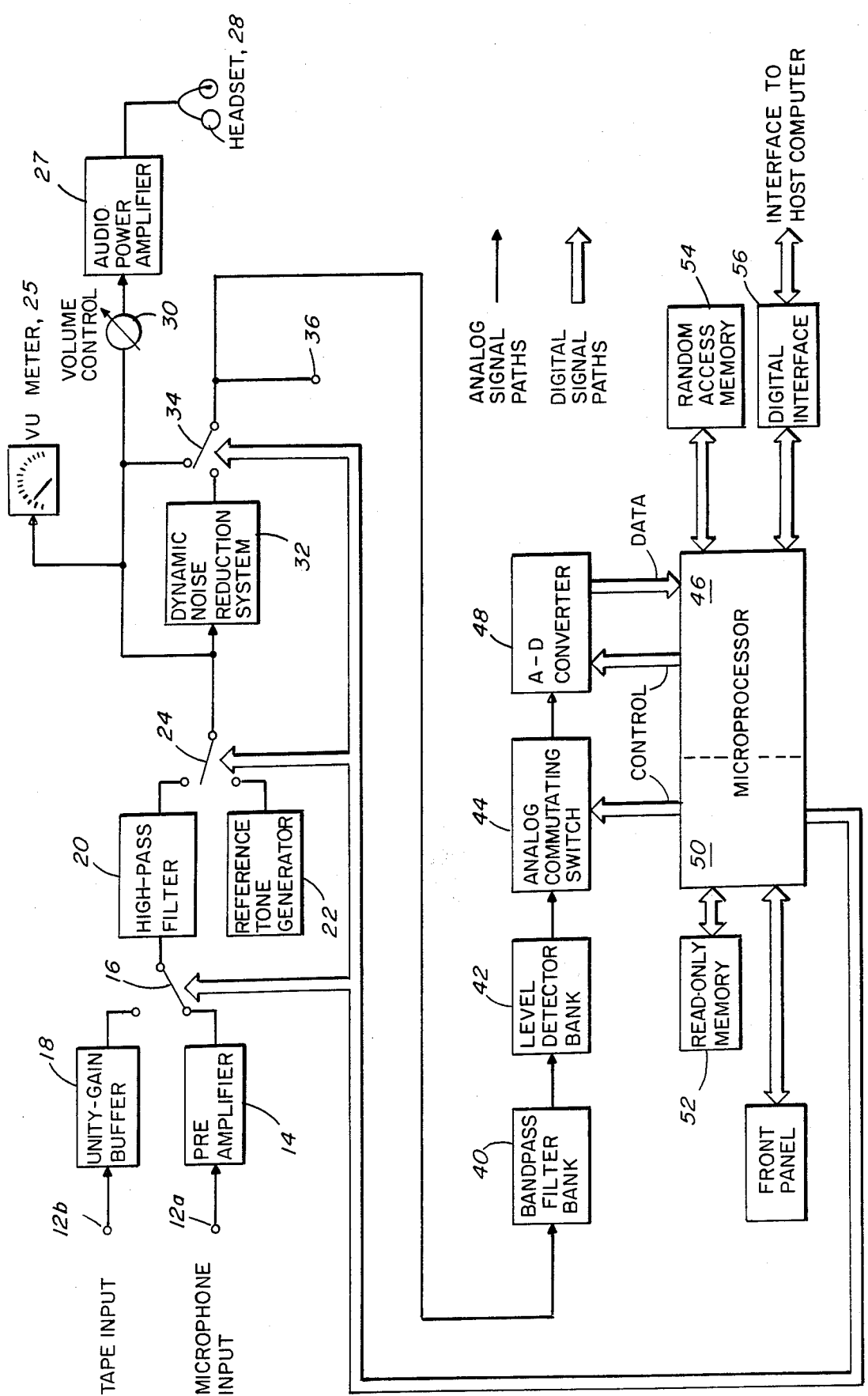
FIG. 1 is a block diagram of one embodiment of an electronic stethoscopic system incorporating the present invention.

In FIG. 1, there is shown an overall block diagram of the accessory package. Stethoscopic data in the form of analog electrical signals is obtained either from a microphonic device or an audio magnetic tape device on which such data has been previously recorded. The basic pick-up transducer preferably has approximately the frequency response and dynamic range of the human ear at low frequencies and further may be provided with detachable input fittings of different contours to match different anatomical areas such as the chest, various joints, the eyes, etc.

In the first case, as seen in FIG. 1, the signal enters via an input jack 12a, is amplified by about 40 dB by a low-noise preamplifier 14, and selected by means of switch 16.

In the second case shown, the signal is conditioned by a unity-gain buffer 18 before being selected by the switch 16. In the preferred embodiment the switch 16, as well as other switches noted hereinafter, are analog electronic switches, allowing computer control of the signal path. The preamplifier 14 is preferably made up of discrete devices, rather than integrated-circuit operational amplifiers, to achieve a lower noise figure.

The signal is then fed to a high-pass filter 20 which reduces the saturation and desensing of the rest of the circuitry caused by low frequency energy in the signal.

A reference tone generator 22 produces a signal of predetermined amplitude, frequency, and spectral composition, for the purpose of calibrating the entire signal processing chain with the exception of the low-noise preamplifier 14 and the high-pass filter 20. The reference tone generator 22 preferably consists of a digital oscillator implemented with CMOS digital circuits and producing a square wave of approximately 400 Hz frequency and 500 mV peak-to-peak amplitude. A switch 24 then selects either the calibration tone or the data signal.

At this point, the signal path is tapped to feed a VU (Volume Unit) meter 24, and a headset audio power amplifier 27, allowing a headset 28 to be used to monitor the incoming audio signal. A volume control 30 is provided to adjust the monitoring level without changing the gain of the signal processing chain.

The main signal path at this point leads to a dynamic noise reduction circuit 32. A commercially available circuit of this type is known as the dbx noise reduction system. The output of the dynamic noise reduction circuit 32 is fed to a bypass switch 34 for use when processing a previously recorded signal which was previously processed through a dynamic noise reduction device. An output jack 36 may be provided to enable recording of the output signal from the dynamic noise reduction circuit 32.

The signal is then fed to a bank of 31 bandpass active filters 40. The center frequencies of these filters are spaced according to the I.S.O. (International Standards Organization) recommendations for audio signal analysis, that is, one-third of an octave starting at 20 Hz and ranging to 20,000 Hz.

Suitable filters for use here are switched-capacitor integrated circuit filter elements, such as the Reticon Model No. R5604. The output of each filter is then fed to one of the level detectors in a level detector bank 42. The output of each level detector is the RMS value of the respective filter's output averaged over a time which depends on the time constant of the particular level detector low-pass filter. A suitable time constant is two times the reciprocal of the center frequency of the respective filter. The center frequency of the lowest filter and the rate of sampling of output values by the digital system is approximately 20 Hz or 50 milliseconds.

The output from each level detector is then fed to a digitally-controlled electronic commutating switch 44. This switch is controlled by a digital signal from a microprocessor 46 which determines the level detector to be sampled at any instant of time. It may be an integrated-circuit electronic analog switch, such as a type 4066 CMOS device. The selected level detector signal is then fed to an integrated circuit analog-to-digital converter 48, which converts the analog signal to a digital value representing its amplitude. Conversion begins under computer control, and a logic signal is affirmed when the conversion is complete. Depending upon the nature of the host computer, this conversion is made with either 8 or 12 bits of precision; e.g., 8 bits for an 8-bit host computer, 12 bits for a 16-bit host computer.

The digitized sampled filter output signal is finally fed to a microprocessor chip 50, such as an Intel 8085, which is also used to control the signal path selector switches 16, 24, and 34; the analog commutating switch 44; and the A/D converter 46. The program required by the microprocessor to perform its functions is stored in a read-only memory 52, and the data acquired is temporarily stored in a random-access memory 54. When sufficient amounts of data have been stored, the microprocessor chip 50 transmits the data to the host microcomputer via a digital interface 56, possibly at a rate different than that at which the data was originally sampled. The interface 56 may be an RS232 serial interface comprising a standard U.A.R.T. (Universal Asynchronous Receiver Transmitter) integrated circuit. A parallel interface may also be used. This same interface is used by the microprocessor 50 to receive commands from the host microcomputer which control the sequencing of the data acquisition process and its transmission to the host.

Also connected to microprocessor 50 are a number of indicator lights and switches making up a "front panel" 58. These lights are energized by the microprocessor 50 to annunciate to the user the state of the data acquisition and transmission sequence. The switches can be manipulated by the user to start the acquisition process (e.g., by means of a foot pedal switch) and/or select optional parameters (e.g., sampling rate, whether to use the dynamic noise reduction circuitry, etc.)

Figure 2:
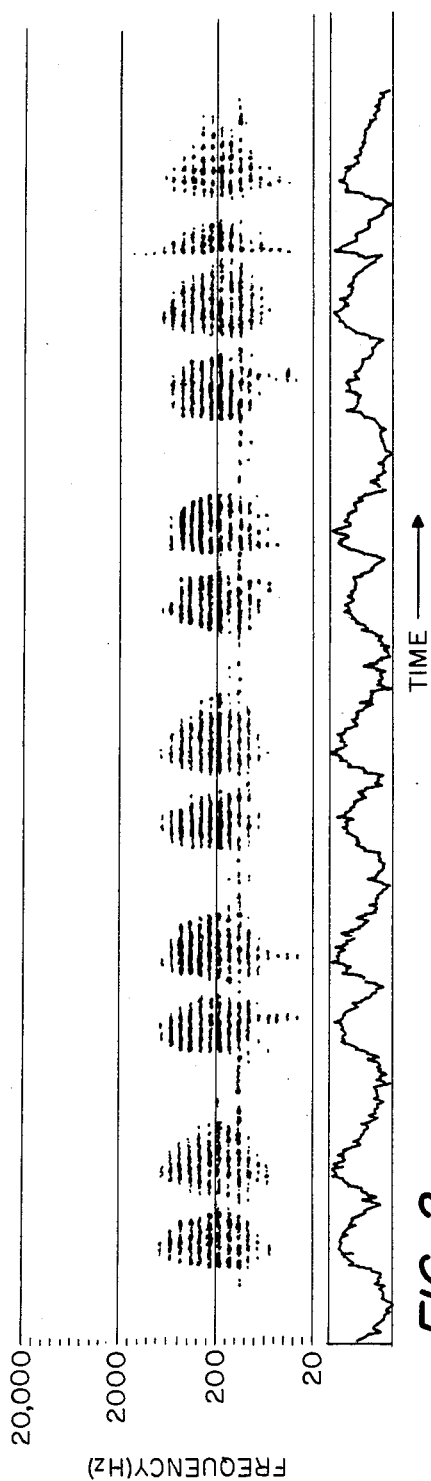
FIG. 2 is a typical display pattern.

The accessory of the present invention can be utilized with any of several available general-purpose microcomputers. The microcomputer may then be programmed to present the data in a variety of forms, both graphical and numeric, on a cathode-ray tube screen, or as printed hard copy. FIG. 2 illustrates a typical fundamental display format which is the same whether presented on the screen or printed. The horizontal or abscissa axis of the display represents time elapsed during the recording of a data sample, the recording commencing at the extreme left of the display and ending at the extreme right. The vertical or ordinate axis of the display consists of several ordinates, each corresponding to a center frequency of one of the filters of the filter bank. The lowest center frequency appears at the bottom of the display and the first frequency at the top of the display.

At each intersection of the horizontal scale (time) and the vertical scale (frequency) a number of dots appear. The dot density is proportional to the output of the corresponding filter at that point in time, with no dots corresponding to a minimum output of that filter and the greatest dot density corresponding to a maximum in the output of that filter at that point in time. The values of that minimum and maximum, as well as the scaling between filter output and dot density, can be controlled to enhance features of the data or eliminate background noise.

The resulting display then appears to the user of the system as a relief or contour map of sound intensity versus frequency and time. Interpretation of the data and correlation with other forms of display is aided by scales in the horizontal and vertical axes. These scales are particularly needed when displaying a reduced time or frequency range at a larger scale in order to amplify details in the display. In addition, the preferred implementation includes a single trace of the rms (root-mean-square) sum of all the filter amplitudes versus time immediately below the main display, in FIG. 2., with the time scale coinciding with that of the main display. The purpose of this auxiliary presentation is to portray the variation of total sound energy with time, and is intended to aid in the interpretation of the sound energy/frequency/time patterns contained in the main display. FIG. 2 represents 768 frames in 13.0 seconds.

Figure 3A:
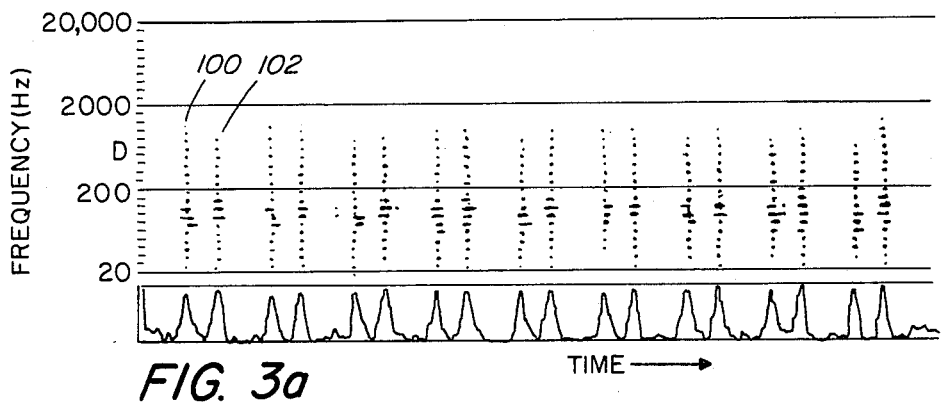
FIGS. 3a–3d are display patterns of various human heart sounds.
Figure 3B:
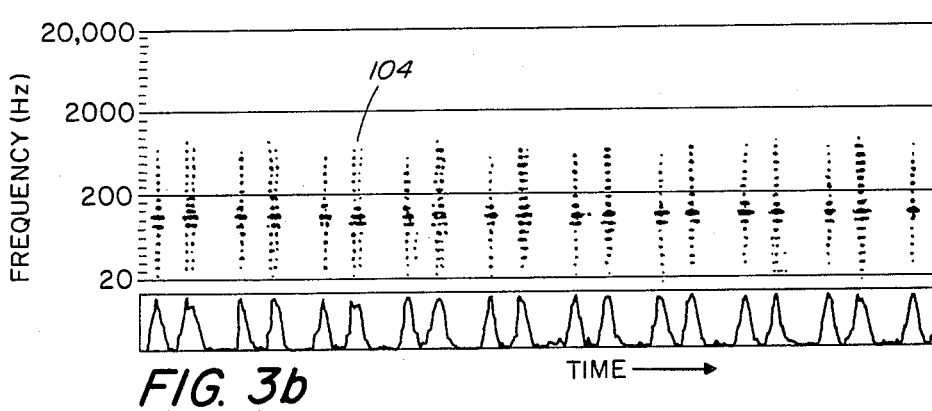
Figure 3C:
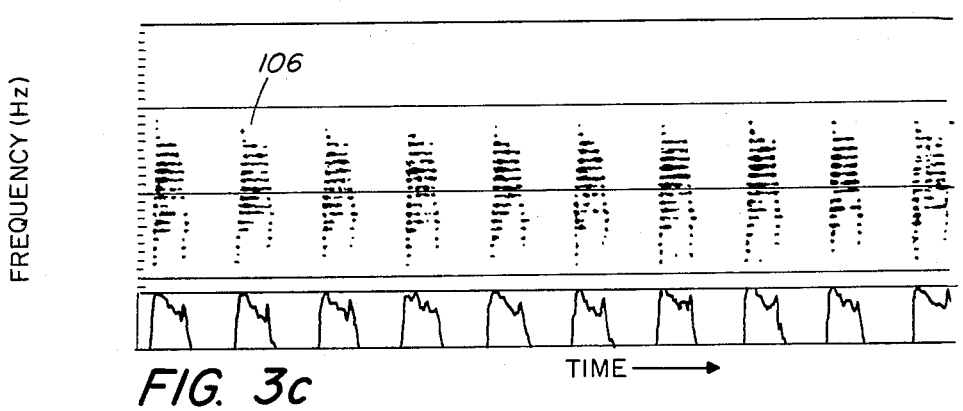
Figure 3D:
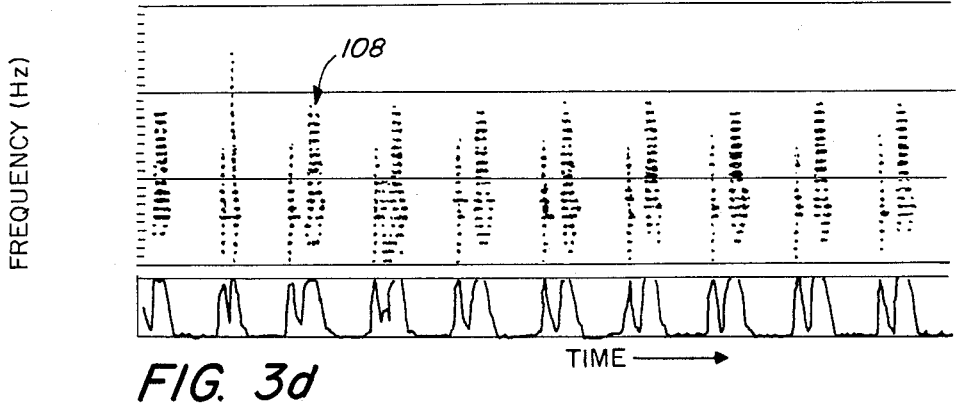

With reference now to FIGS. 3a-3d, heart sounds are analyzed in accordance with the present invention. FIG. 3a illustrates normal heart beat sounds, with systolic sounds represented at 100 and diastolic sounds at 102. FIG. 3b illustrates a medical condition known as right bundle branch block. In this condition, the diastolic sound is split as clearly shown at 104. A condition known as decrescendo murmur is shown in FIG. 3c. This murmur condition shown at 106 decreases blood flow entering into diastole. Finally, FIG. 3d illustrates the patterns resulting from a condition known as late systolic crescendo murmur. Note that the second heart sound 108 is thicker indicative of increased blood flow into diastole. It can thus be seen that the present invention results in patterns which correlate with known heart anomalies.

Figure 4A:
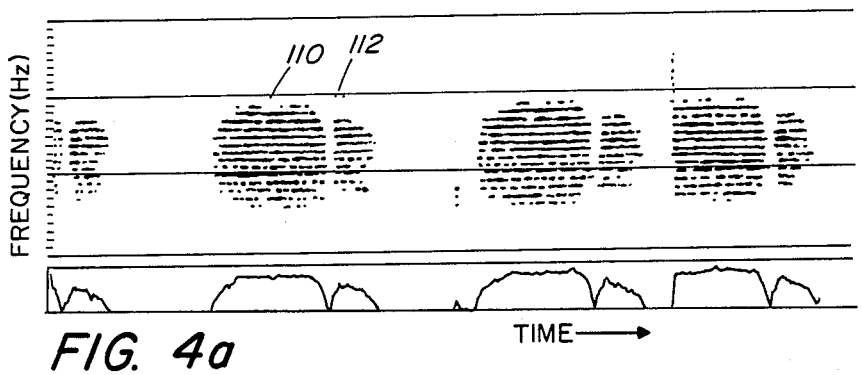
FIGS. 4a–4c are display patterns of various human lung sounds.
Figure 4B:
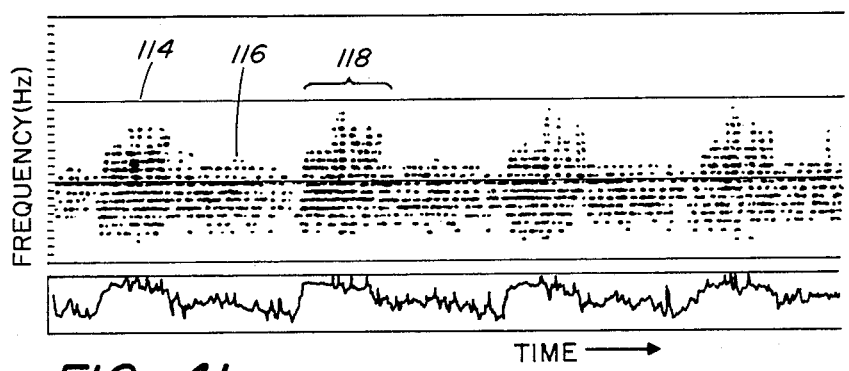
Figure 4C:
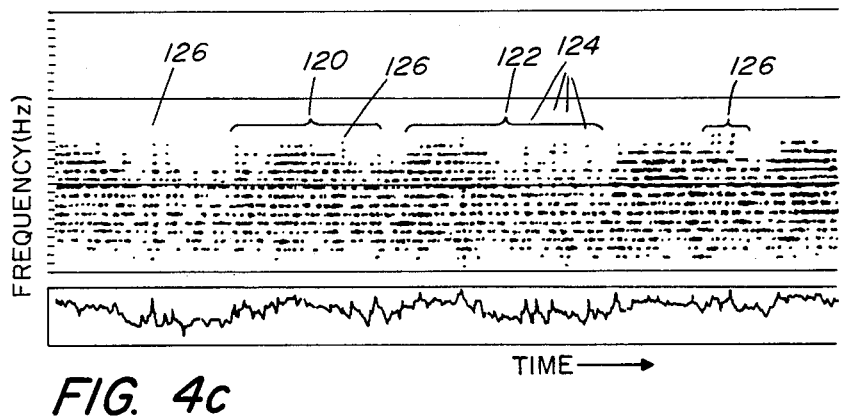

FIGS. 4a-4c illustrate the use of the present invention for the analysis of lung sounds. FIG. 4a represents the patterns generated by normal lungs with inspiration at 110 and expiration at 112. FIG. 4b illustrates the patterns resulting from asbestosis. In this figure, inspiration is shown at 114 and expiration at 116. Late inspiratory rales is shown at 118. The patterns associated with another medical condition, cronic obstructive lung disease, is shown in FIG. 4c. Inspiration is shown at 120 and expiration at 122. Late expiratory rales are shown at 124. In addition, continuous ronchi such as at 126 can be seen throughout FIG. 4c.

An alternative display also available in the preferred embodiment of the invention is a three-dimensional perspective version of the basic display format described above. In this version, time and frequency are the longitudinal and transverse dimensions, respectively, of a flat horizontal rectangle drawn in perspective. The output of each filter at each point in time is indicated as a vertical distance above this rectangle over the corresponding time/frequency intersection. All the points measured at a given instant (that is, a sample including all the filters' outputs) are corrected by straight line segments. A "hidden line removal" process eliminates from the display those points—and those line segments connecting them—that would not be seen if the resulting shape were to define a solid body. Thus, the resulting perspective display appears to be that of a three-dimensional opaque surface, such as a mountain range.

Figure 5:
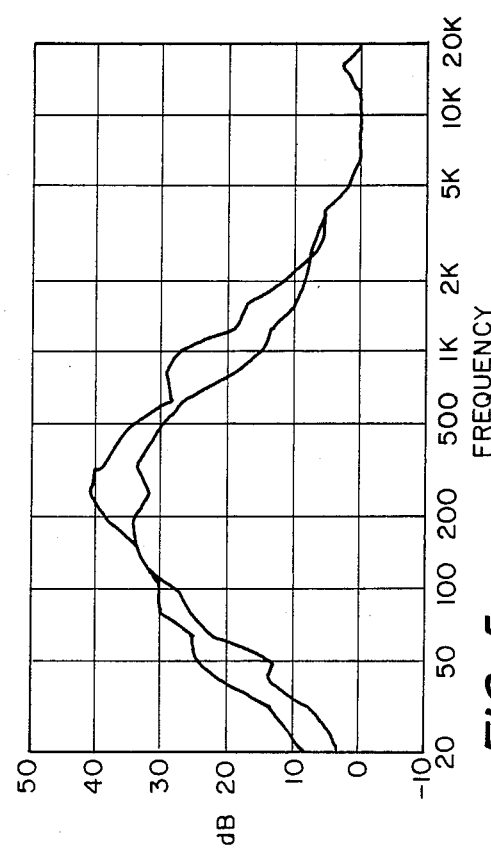
FIG. 5 is an alternate display of lung sound patterns.

A third display device allows the user to select individual instants in time, and view on the screen, or print on paper, the output of all the filters at that time, with filter center frequency measuring from left to right on the horizontal axis and filter output increasing from bottom to top in the vertical direction. Such a display is shown in FIG. 5 illustrating two breath sounds. In addition to being able to select those individual "cross-sections" of the data, the user can collect a number of cross-sections in sets, average the sets, subtract one cross section from another or from an average, or subtract an average from a cross-section. A particularly useful feature of this display option is the capability of comparing data from different samples, including averages from a large number of data recordings.

Understanding of the system illustrated in FIG. 1 and the typical display shown in FIG. 2 may be facilitated by a consideration of the software specifications. As noted above, the invention, (hereinafter the "CSA" for computerized stethoscopy accessory), is a peripheral for use with any of several commercially available general purpose microcomputers.

As noted with reference to FIG. 1, the CSA includes the bank of 31 third-octave bandpass filters 40, a computer-controlled analog selector switch 44, and an 8-bit A/D converter 48. The local microprocessor 46 controls the recording of the output of the analog-to-digital converter (A/D) 48. This output, in the form of a number of frames of 31 1-byte unsigned numbers each, is stored in the CSA's local memory. The CSA's microprocessor 50—hereinafter referred to as the CSAM—communicates with the host computer via the interface 56, receiving commands from the host and sending data back to the host. In particular, the host commands the CSA's recording of the data into its local memory, and the subsequent uploading of the data to the host via the same interface 56. The reason for this arrangement is that the data may be recorded at rates that exceed the bandwidth of a conventional serial line.

The CSA's configuration is likewise controlled by the host; in particular, selection of the signal source (microphone or tape input jacks), injection of a calibration tone, and use of a dynamic range expansion circuit (e.g., dBX), are performed by means of electronic switches controlled by the CSAM. A number of "front panel" switches are provided for user control of the configuration. The CSAM senses the pressing of these switches (e.g, by vectored interrupts), communicates the events to the host, and the host then sends the necessary commands to the CSAM to close the required electronic switches.

This arrangement allows the host computer to exercise complete control over the recording conditions; it would be then impossible for a recording made with the dBX in to be labelled "no dBX", as would be the case with manual dBX selection. Even more important, configuration changes could be disabled during the recording process, and standard configurations can be set up automatically (e.g. with a calibration tone at the beginning) without any changes in the CSAM code. An alternative is not to have any hardware front panel switches at all, but allow "manual" control of the CSA configuration from a host computer menu.

As a minimum, there should be a single "attention" input on the CSA; this input may be connected to a momentary contact pushbutton on the pick-up itself. With the CSA/host, system on "ready to record", this switch will be used to signal initiation of the recording process; a second actuation before the recording is completed can be used to "abort" the recording (if, for instance, an extraneous noise occurs). Implied is the need for this input to be active (interrupt or fast polling) during the recording process. Finally, a number of LED's are used to indicate the state of the CSA, in particular the "recording in progress" state.

The recording process itself requires the CSAM to commutate the selector switch over the 31 filters, command an A/D conversion at each position, read the output of the A/D converter, and store the resulting number in successive locations in the CSAM local memory. The number of samples to record, subject to memory size limits, is determined by a host computer command. It would also be desirable to have the sampling rate being the limit of the CSA hardware (A/D settling time and/or CSAM sampling speed), and the lowest rate being approximately equal to the center frequency of the lowest filter in the filter bank, i.e., 20 hz or 20 frames/sec., (1 frame=all 31 filter outputs). Since a frame requires 31 bytes, it should be possible to store some 1800 frames in the CSAM's memory, allowing 8k for ROM, I/O address space, etc. This assumes an 8-bit CSAM with a 64k address space limit.

The recording process should have a "data-out" feature: if the data inputted consists of more than TBD frames of all zeros (indicating perhaps a break in the analog signal path), the recording process should be aborted and the host notified.

The CSAM should have two states: standby and record. Upon completion of the power-up activity, which should include a ROM checksum and RAM write/read check, the unit enters the standby mode. In this mode, the CSA waits for commands from the host, including entering the recording mode.

In the recording more the CSAM sequences the electronic commutator, enables the A/D converter, and stores the data in its RAM; any data coming from the host will abort the recording, and the unit shall enter the standby mode. If the recording completes without aborting, the unit enters automatically the standby mode. Different messages are sent to the host in each Among the host commands accepted by the CSAM in standby mode is the transmission of a frame (31 numbers), preceded by the frame member and followed by a checksum; the host can then request retransmmission of an incorrectly received frame.

Specification Data
CSAM input/output

1. RS 232 bidirectional to/from host computer, max rate 19,200 baud.
2. RMRA (Record More Request/Abort)—1 bit discrete input: requests host to begin recording (in standby mode), aborts recording (direct, not via host) in recording mode.
3. SRCS (Source Select)—1 bit discrete output: controls the electronic switch that selects the signal source (microphone jack or tape jack); when active selects the microphone input.
4. NRCE (Noise Reduction Circuit Enable)—1 bit discrete output: when active, enables the Noise Reduction Circuitry.
5. CALT (Calibration Tone)—1 bit discrete output: when active, a known amplitude and frequency tone is injected in the analog signal path.
6. RECA (Recording mode Announciator)—1 bit discrete output: controls an LED to indicate to the user that a recording is in process.
7. RDYA (Ready to record Announciator)—1 bit discrete output: controls an LED to indicate to the user that the system is ready to record.
8. FLTR (Filter select)—5 bit discrete output: selects the filter whose output will be fed to the A/D converter; a value of 1 selects the lowest frequency filter, whereas a value of 20 (hex) selects the 31st (highest frequency) filter. Use of the zero value is TBD.
9. CONV (Conversion enable)—1 bit output: when transitioning from the inactive to the active state, starts the A/D conversion process (better check against the requirements of the A/D chip used).
10. DATA (Data input)—8 bit input: the value produced by the A/D chip.

The above assumes that timing of the conversion is by software, that is, the CSAM waits a predetermined number of processor cycles between asserting CONV and reading DATA.

Messages in STANDBY mode from host to CSAM

Note: The following messages have either no arguments, a single byte argument, or a two byte argument, indicated by NN or NNNN in the following table.
1. RESET (Reset)—Forces a cold-start of the CSAM software, including the power-up self-tests.
2. NRSEL (Noise Reduction Select)—Selects the Noise Reduction circuitry.
3. NRDES (Noise Reduction Deselect)—Deselects the Noise Reduction circuitry.
4. MIKEI (Microphone Input)—Selects the microphone input jack.
5. TAPEI (Tape Input)—Select the tape input jack.
6. TONEB (Tone Begin)—Begin injecting calibration tone.
7. TONEE (Tone end)—End injecting calibration tone.
8. RDYON (Ready on)—Activate the "ready to record" announciator.
9. RDYOF (Ready off)—Deactivate the "ready to record" announciator.
10. SMPRT NN (Sample rate select)—Sets the sampling rate. The encoding of the argument byte is TBD.
11. RECLN NNNN (Record a number of frames)—Starts the recording process; unless terminated by the CSA's discrete input, NNNN frames will be recorded.
12. TXFRM NNNN (Transmit Frame Number)—Requests the transmission of the specified frame number, preceded by the frame number (again), and followed by a checksum byte; the checksum method is TBD.

Messages in STANDBY mode from CSAM to host

1. RDYOK (Ready to operate, all self-tests O.K.)—CSA's answer to the autobauding sequence if all power-up tests are positive. Similar answer for the RESET command.
2. PUERR NN (Power-up error)—CSA's answer to the autobauding sequence if power-up self-test NN is negative.

Messages in RECORD mode from CSAM to host

1. RENDN NNNN (Recording end and number) - End of the recording process; a value of NNNN of zero indicates a data-out condition was encountered (more than TBD frames of all zero data). A value of NNNN different from that specified in the TXFRM command from the host indicates that the recording process was stopped by the CSA's hardware signal.

It is thus seen that the objects of this invention have been achieved in that there has been disclosed method and apparatus for identifying specific medical conditions from detected stethoscopic sounds. The sounds are processed electronically and time variations of the spectral composition of the sounds are displayed in various formats. As discussed above, the displayed patterns correlate with known medical conditions. The invention disclosed herein avoids the use of fast fourier transform techniques so that microcomputers can be used.

What is claimed is:
1. A computerized stethoscopy accessory for use with a host computer comprising means for detecting sounds in a living body, means for converting said detected sounds to electrical signals, a bank of fixed-center-frequency filters having a range of center frequencies from a lowest to a highest frequency, means for applying said electrical signals to said bank of fixed-center-frequency filters, means for sampling the output of each said filter at a rate at least twice the fixed center frequency of the lowest frequency filter of said bank, an analog-to-digital converter connected to said bank of filters for converting the sampled output of each said filter to digital form, means for processing said sampled outputs in said host computer, and an output device connected to said host computer for displaying said sampled outputs in a predetermined format after processing thereof.
2. A computerized stethoscopy accessory as defined in claim 1 wherein the predetermined formed includes the representation of elapsed time on a first axis, the representation of the center frequencies of the filters of the filter bank on a second axis perpendicular to said first axis, and a representation of quantities of sound energy at the intersections of said first and second axes.
3. A computerized stethoscopy accessory as defined in claim 2 wherein the predetermined format further includes a graph of the root mean square sum of all the filter amplitudes versus time.

* * * * *